United States Patent
Khosla et al.

(10) Patent No.: US 9,489,596 B1
(45) Date of Patent: Nov. 8, 2016

(54) OPTIMAL RAPID SERIAL VISUAL PRESENTATION (RSVP) SPACING AND FUSION FOR ELECTROENCEPHALOGRAPHY (EEG)-BASED BRAIN COMPUTER INTERFACE (BCI)

(71) Applicant: HRL Laboratories, LLC, Malibu, CA (US)

(72) Inventors: Deepak Khosla, Camarillo, CA (US); Matthew S. Keegan, Santa Monica, CA (US); Kevin R. Martin, Oak Park, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 14/565,094

(22) Filed: Dec. 9, 2014

Related U.S. Application Data (60) Continuation-in-part of application No. 14/185,908, filed on Feb. 20, 2014, now Pat. No. 9,269,027, which is a division of application No. 12/975,352, filed on Dec. 21, 2010, now Pat. No. 8,699,767, application No. 14/565,094, which is a continuation-in-part of application No. 14/206,421, filed on Mar. 12, 2014.

(60) Provisional application No. 61/779,258, filed on Mar. 13, 2013.

(51) Int. Cl.
 *G06K 9/62* (2006.01)
(52) U.S. Cl.
 CPC .................. *G06K 9/6263* (2013.01)
(58) Field of Classification Search
 CPC ............... G06K 9/00496; G06K 9/46; G06K 2009/4666; G06K 9/4671; G06K 9/4676; G06K 9/6267; G06K 9/80; G06T 2207/20021
 See application file for complete search history.

(56) References Cited

U.S. PATENT DOCUMENTS

| | | | |
|---|---|---|---|
| 6,670,963 B2 | 12/2003 | Osberger | 345/629 |
| 7,139,006 B2 | 11/2006 | Wittenburg et al. | 345/679 |
| 7,835,581 B2 | 11/2010 | Mathan et al. | 382/224 |
| 8,214,309 B1 | 7/2012 | Khosla et al. | 706/14 |
| 8,285,052 B1 * | 10/2012 | Bhattacharyya et al. | 382/190 |
| 8,335,751 B1 | 12/2012 | Daily et al. | 706/14 |

(Continued)

FOREIGN PATENT DOCUMENTS

WO    WO 03/093947 A2    11/2003

OTHER PUBLICATIONS

Rajan Bhattacharyya, Deepak Khosla, David Huber, Penn Tasinga, "Optimal Image Ordering for Rapid Serial Visual Presentation Using Electroencephalography," SIN NeuroScience 2009, Oct. 17-21, Chicago, Poster Presentation, (2009).

(Continued)

*Primary Examiner* — Andrew W Johns
(74) *Attorney, Agent, or Firm* — Tope-McKay & Associates (57) ABSTRACT

Described is system for optimizing rapid serial visual presentation (RSVP) spacing and fusion. The system receives a sequence of a plurality of rapid serial visual presentation (RSVP) image chips. The plurality of RSVP image chips are generated from an image via a pre-processing step and have a high probability of containing a target of interest. The system alters the order of the sequence of the plurality of RSVP image chips to increase the probability of detection of a true target of interest when presented to a human subject.

19 Claims, 8 Drawing Sheets

(56) References Cited

U.S. PATENT DOCUMENTS

| | | |
|---|---|---|
| 8,374,687 B2 | 2/2013 | Mathan et al. ............... 600/544 |
| 8,483,816 B1 | 7/2013 | Payton et al. ................ 600/544 |
| 2005/0047647 A1 | 3/2005 | Rutishauser et al. ......... 382/159 |
| 2007/0173699 A1 | 7/2007 | Mathan et al. ............... 600/300 |
| 2007/0236488 A1 | 10/2007 | Mathan et al. ............... 345/418 |
| 2008/0056611 A1 | 3/2008 | Mathan et al. ............... 382/284 |
| 2009/0136098 A1* | 5/2009 | Mathan et al. ............... 382/128 |
| 2010/0280403 A1 | 11/2010 | Erdogmus et al. ........... 600/545 |
| 2012/0089552 A1 | 4/2012 | Chang et al. .................. 706/52 |
| 2012/0172743 A1 | 7/2012 | Aguilar et al. ............... 600/544 |

OTHER PUBLICATIONS

Deepak Khosla, David J. Huber, Rajan Bhattacharyya, Mike Daily, Penn Tasinga, "Neurally Inspired Rapid Detection of Sparse Objects in videos," Signal Processing, Sensor Fusion, and Target Recognition XIX, Proc. of SPIE vol. 7697, 76971C, (2010).

Steven B. Most, Marvin M. Chun, David M. Widders and David H. Zald. "Attentional rubbernecking: Cognitive control and personality in emotion-induced blindness", Psychonomic Bulletin & Review, (2005) vol. 12, No. 4, 654-661, DOI: 10.3758/BF03196754.

Bernhard Hommel and Elkan G. Akyüre; Lag-1 sparing in the attentional blink:Benefits and cost of integrating two events into a single episode, The Quarterly Journal of Experimental Psychology (2005), 58A (8), 1415-143.

Nieuwenhuis S, Gitzenrat MS, Holmes BD, Cohen JD (Aug. 2005) "The role of the locus coeruleus in mediating the attentional blink: a neurocomputational theory", J Exp Psychol Gen 134 (3): 291-307, doi:10.1037/0096-3445.134.3.291. PMID 13131265.

Sun, Y., et al., "Probabilistic judgment by a coarser scale: behavioral and ERP evidence," in Proceedings of the Twenty-sixth Annual meeting of the Cognitive Science Society, 2004.

Thorpe, S., et al., "Speed of processing in the human visual system," Nature, vol, 381, pp. 520-522, 1996.

University of California, San Diego Complex Systems and Cognition Laboratory, CSCLAB Image Database http://csclab.ucsd.edu/labeledimages.php, 2006.

Walther D., et al, "Attentional selection for object recognition—a gentle way," Lecture Notes in Computer Science 2525: 472-479, 2002.

Wolfe J.M. "Visual Search in continuous, naturalistic stimuli," Vision Research 34: 1187-1195, 1994.

Vazirani, , "Approximation Algorithms," Springer-Verlag, Berlin, Germany. pp. 32-33 (2004).

Vogel. E.K., et al., "The Visual NI Component as an index of a discrimination process" Psychophysiology. 2000.

Yamaguchi, S., et al., "Cerebral Asymmetry of the 'Top-down' allocation of attention to global and local features," The Journal of Neuroscience, 20, 1-5, 2000.

Zang H., et al., "SVM-KNN: Discriminative nearest neighbor classification for visual category recognition," CVPR 2006.26

Vazirani, V., "Approximation algorithms," Springer-Verlag, Berlin, Germany, p. 32, 2004.

http://en.wikipedia.org/Travelling_salesman_problem, Dec. 2, 2009.

Richard P. Wildes. "A measure of motion salience for surveillance applications" in Proc. IEEE Int'l Conf. Image Processing,1998.

Thorpe, et al., "Speed of Processing in the Human Visual System", Nature. vol. 381, pp. 520-522, 1996.

Khosla, et al., "Optimal detection of objects in images and videos using elecroencephalography (EEG)," Proc SPIE 8050, Signal Processing, Sensor Fusion, and Target Recognition XX, edited by Ivan Kadar, Proc. of SPIE vol. 8050 (May 4, 2011).

Raymond, et al., "Temporary suppression of visual processing an RSVP task: an attentional blink?" Journal of experimental psychology. Human perception and performance 18 (3): pp. 849-860, 1992.

Andoni A., et al., "Near-Optimal Hashing Algorithms for Near Neighbor Problem in High Dimensions," Proceedings of the Symposium on Foundations of Computer Science (FOCS'06), 2006.

Bentin, S., et al., "Electrophysiological studies of face perception in humans," Journal of Cognitive Neuroscience. 8. 551-565, 1996.

Berg A., "Shape matching and object recognition," Ph.D thesis, UC Berkeley, Computer Science Division, Berkeley, CA, Dec. 2005.

Berke, C., et al., "Evaluation of an EEG-workload model in an aegis simulation environment" in Proceedings of SPIE Defense and Security Symposium, 90-99, 2005.

Bhattacharyya, R., et al., "Optimal image ordering for rapid serial visual presentation using electroencephalography," Presented at Society of NeuroScience (SfN) annual meeting, Chicago, 2009.

Carpenter G.A., et al., "A massively parallel architecture for a self-organizing neural pattern recognition machine," Computer Vision, Graphics, and Image Processing, 37, 54-115, 1987.

Carpenter G.A., et al., "The what-and-where filter a spatial mapping neural network for object recognition and image understanding," Computer Vision and Image Understanding, 69, 1-22, 1998.

Carpenter G.A., "Default ARTMAP," in Proc. of the International Joint Conference on Neural Networks (IJCNN'03), 1396-1401, 2003.

Carpenter G.A., et al,, "Self-organizing information fusion and hierarchical knowledge discovery: a new framework using ARTMAP neural networks," Neural Networks, 18, 287-295, 2005.

Cowell, et al., "Construction and validation of neurophysio-technological framework for imagery analysis," in J.Jacke (Ed.): Human-Computer Interaction, Part II, HCII 2007, LNCS 4551, pp. 1096-1105, 2007, © Springer-Verlag Berlin Heidelberg.

Draper B., et al., "Evaluation of Selective Attention under Similarity Transforms," In Workshop on Performance and Attention in Computer Vision. Graz, Austria, Apr. 2003.

Eckhom R., et al., "Coherent Oscillations: A Mechanism of feature linking in the visual cortex?" Biological Cybernetics 60, 121-130, 1988.

Eimer, M., "Does the face-specific N170 component reflect the activity of a specialized eye processor?" Neuroreport, 9, 2945-2948, 1998.

Fabre-Thorpe, M., et al , "A limit to the speed of processing in Ultra-Rapid visual categorization of novel natural scenes." Journal of Cognitive Neuroscience, 13, 171-130, 2001.

Field D.J. "Relations between the statistics of natural images and the response properties cortical cells," J. Opt. Soc. Am. A., 4: 2379-2394, 1987.

Fei-Fei L., et al., "Learning generative visual models from few training examples: an incremental Bayesian approach tested on 101 object categories," CVPR 2004, Workshop on Generative-Model Based Vision, 2004.

Gerson, A.D., et al., "Cortically coupled computer vision for rapid image search," IEEE Transactions Neural Systems and Rehabilitation Engineering, 14(2): 174-179, Jun. 2006.

Gladwell M., "Blink: the power of thinking without thinking," 1st ed. Little, brown and company: Time Warner Book Group, New York, 2005, pp. 18-47.

Gutin, G., et al., "Traveling salesman should not be greedy: domination of analysis of greedy-type heuristics for the TSP," Discrete Applied Mathematics, 117: 81-86, 2002.

Gray C.M., et al., "Oscillatory Responses in Cat visual cortex exhibit intercolumnar synchronization which reflects global stimulus properties," Nature 338:334-336. 1989.

Hopf, J.-M., et al., "Localizing visual discrimination processes in time and space," The American Physiological Society, 88, 2088-2095, 2002.

Itti L., et al., "A saliency-based search mechanism for overt and covert shifts of visual attention," Vision Research, 40: 1489-1506, 2000.

Itti L., et al., "A Model of Saliency-Based Visual Attention for Rapid Scene Analysis," IEEE Transactions on Pattern on Analysis and Machine Intelligence, 20, 1254-1259, 1998.

Itti L., et al., "Bayesian Surprise Attracts Human Attention," Vision Research 49: 1295-1306, 2008.

Itti, L., et al., "Computational Modeling of Visual Attention," Nature Reviews Neuroscience, 2, 194-203, 2001.

Itti, L., "Quantifying the Contribution low-level saliency to human eye movements in dynamic scenes," Visual Cognition, 12, 1093-1123, 2005.

(56) References Cited

OTHER PUBLICATIONS

Keysers, C., et al., "The Speed of Sight," Journal of Cognitive Neuroscience, 13(1), 90-101, 2001.

Khosla D., et al., "Bio-Inspired Visual Attention and Object Recognition," In: Proc. SPIE Defense, Security, and Sensing. 6560, 656003, 2007.

Khosla. D., et al., "A bio-inspired system for spatio-temporal recognition in static and video imagery," Proc. SPIE 6560, 656002, 2007.

Koch C., et al., "Shifts in selective visual attention: towards the underlying neural circuitry," Human Neurobiology, 4: 219-227, 1985.

Lazebnik S., et al., "Beyond Bags of Features: spatial pyramid matching for recognizing natural scene categories," In: Proc. IEEE Conference on Computer Vision and Pattern Recognition (CVPR), 2006.

Ling, H., et al., "Diffusion distance for histogram comparison," IEEE Computer Society Conference on Computer Vision and Pattern Recognition (CVPR), 2006.

Medasani, S. et al., "Possibilistic particle swarms for optimization," Proceedings 5673 of SPIE/IST Symposium on Electronic Imaging, 2005.

Medasani, S., et al., "Active learning system for object fingerprinting," International Joint Conference on Neural Networks, 2004.

Morrison, D., et al., "Semantic clustering of images using patterns of relevance feedback," in Proceedings of the 6th International Workshop on Content-based Multimedia Indexing (CBMI 2008), London, UK.

Nane S.A., et al., "Columbia Object Image Library (COIL-100)," Technical Report CUCS-006-96, Feb. 1996.

Navalpakkam V., et al., Modeling the influence of Task on Attention. Vision Research, 45: 205-231, 2005.

Navalpakkam V., et al., "An integrated model of top-down and bottom-up attention for optimal object detection," In: Proc. IEEE Conference on Computer Vision and Pattern Recognition (CVPR), 1-7, 2006.

Navalpakkam V., et al., "Sharing resources: buy attention, get recognition," In: Proc. International Workshop on Attention and Performance in Computer Vision (WAPCV'03), Graz, Austria, Jul. 2003.

Navalpakkam, V, et al., "Search goal tunes visual features optimally," Neuron, 53, 605-617, 2007.

Niebur E., at al., "Control of selective visual attention: modeling the 'where' pathway," In D Touretzky, M Mozer and M. Hasselmo. Neural Imformation Processing Systems (NIPS 8), 802-808, Cambridge, MA, MIT, Press 1996.

Orabona F., et al., "Object-based Visual Attention: A Model for a Behaving Robot," In 3rd International Workshop on Attention and Performance in Computational Vision (in CVPR 2005). San Diego, CA, Jun. 2005.

Owechko, Y., et al., "A swarm-based volition/attention framework for object recognition:" IEEE Conference on Computer Vision and Pattern Recognition. San Diego, 2005.

Owechko, Y., et al., "Cognitive swarms for rapid detection of objects and associations in visual imagery," IEEE Swarm Intelligence Symposium, 2005.

Peters, R.J., et al., "Beyond bottom-up: Incorporating task-dependent influences into computational model of spatial attention," in: Proc. IEEE Conference on Computer Vision and Pattern Recognition (CVPR), 2007.

Rogowitz B.E., et al., "Perceptual image similarity experiments," Proceedings of SPIE, 3299: 576-590, 1998.

Scholl B.J., "Objects and Attention: the state of the art," Cognition 80, 1-46, 2001.

Serre T., et al., "Object recognition with features inspired by visual cortex," in Proceedings of the IEEE conference on computer vision and pattern recognition (CVPR), San Diego, CA, Jun. 2005.

Smeulders, A., et al., "Content-based retrieval at the end of the early years," IEEE Transactions PAMI, 22 (12): 1349-1380, 2000.

Sun Y., et al., "Hierarchical selectivity for object-based visual attention," Submitted to Artificial Intelligence, 2004.

Notice of Allowance for U.S. Appl. No. 12/975,352, Dated mailed: Dec. 5, 2013.

Notice of Allowance for U.S. Appl. No. 14/185,908, Date mailed Oct. 15, 2015.

Office Action 1 for U.S. Appl. No. 12/975,352, Dated mailed Jul. 23, 2013.

Response to Office Action 1 for U.S. Appl. No. 12/975,352, Dated mailed Aug. 21, 2013.

Office Action 2 for U.S. Appl. No. 12/975,352, Date Mailed: Sep. 25, 2013.

Sajda et al. (Mar. 2003) "High-throughput image search via single-trial event detection in a rapid serial visual presentation task." Proc. 1st Int'l IEEE EMBS Conf. on Neural Engineering, pp. 7-10.

Khosla et al. (2011) "Optimal detection of obects in images and videos using electroencephalography (EEG)." SPIE vol. 8050, Article 80501 C.

Einhauser et al. (2007) "A bottom-up model of spatial attenton predicts human error patterns in rapid scene recognition." J. Vision, vol. 7 No. 10, Article 6, pp. 1-13.

Response to Office Action 2 for U.S. Appl. No. 12/975,352, Date mailed: Nov. 25, 2013.

Office Action 1 for U.S. Appl. No. 14/206,421, Date mailed: Dec. 24, 2015.

\* cited by examiner

OPTIMAL RAPID SERIAL VISUAL PRESENTATION (RSVP) SPACING AND FUSION FOR ELECTROENCEPHALOGRAPHY (EEG)-BASED BRAIN COMPUTER INTERFACE (BCI)

CROSS-REFERENCE TO RELATED APPLICATIONS

This is a Continuation-in-Part application of U.S. Non-Provisional application Ser. No. 14/185,908, filed in the United States on Feb. 20, 2014, entitled, "A System for Optimal Rapid Serial Visual Presentation (RSVP) from User-Specific Neural Brain Signals", which is a Divisional application of U.S. Non-Provisional application Ser. No. 12/975,352, filed in the United States on Dec. 21, 2010, entitled, "A System for Optimal Rapid Serial Visual Presentation (RSVP) from User-Specific Neural Brain Signals", now issued as U.S. Pat. No. 8,699,767.

This is ALSO a Continuation-in-Part application of U.S. Non-Provisional application Ser. No. 14/206,421, filed on Mar. 12, 2014, entitled, "Visual Attention Distractor Insertion for Improved EEG RSVP Target Stimuli Detection", which is a Non-Provisional patent application of U.S. Provisional Application No. 61/779,258, filed in the United States on Mar. 13, 2013, entitled, "Visual Attention Distractor Insertion for Improved EEG RSVP Target Stimuli Detection."

GOVERNMENT LICENSE RIGHTS

This invention was made with government support under U.S. Government Contract Number W31P4Q-08-C-0264 issued by DARPA. The government has certain rights in the invention.

FIELD OF INVENTION

The present invention relates to a system for rapid object detection and, more particularly, to a system for rapid object detection that optimizes rapid serial visual presentation (RSVP) spacing and fusion.

BACKGROUND OF THE INVENTION

Rapid serial visual presentation (RSVP) measures the brain activity of a human subject while watching a stream of rapid images in order to find incongruities and inconsistencies in the images (i.e., "targets"). The RSVP protocol has recently been used as a powerful tool for high-throughput filtering of images into simple "target" and "non-target" categories as described by Thorpe et al. in "Speed of Processing in the Human Visual System" in Nature, vol. 381, pp. 520-522, 1996 (see the List of Incorporated Cited Literature References. Literature Reference No. 3). During a RSVP experiment, the images presented to the human subject are typically randomized.

Khosla et al. (see Literature Reference No. 1) identified that presentation order in RSVP sequences is important in determining brain computer interface (BCI) performance; however, no known works take target spacing in RSVP into consideration. Algorithms in previous systems assume that target chips are streamed to the operator infrequently. This has the disadvantage of potentially allowing targets to be presented at frequencies too high to elicit a detectable evoked response potential (ERP), such as the P300, in the operator.

Thus, a continuing need exists for a system that reduces periods of high frequency target presentation both for the case in which an estimate of the likelihood of target information given a specific image chip is present, and in the case in which such information is absent.

SUMMARY OF THE INVENTION

The present invention relates to a system for rapid object detection and, more particularly, to a system for rapid object detection that optimizes rapid serial visual presentation (RSVP) spacing and fusion. The system comprises one or more processors and a memory having instructions such that when the instructions are executed, the one or more processors perform multiple operations. The system receives a sequence of a plurality of rapid serial visual presentation (RSVP) image chips having an order, wherein the RSVP image chips are generated from an image via a pre-processing step and have a high probability of containing a target of interest. The system then alters the order of the sequence of the plurality of RSVP image chips to increase the probability of detection of a true target of interest when presented to a human subject.

In another aspect, if a posterior probability of a RSVP image chip containing a target of interest is known, then the system removes the RSVP image chip from the sequence of the plurality of RSVP image chips if the posterior probability of the RSVP chip is equal to or above a predetermined threshold.

In another aspect, the predetermined threshold is set according to a permissible false positive rate.

In another aspect, the system performs N staggered raster scans of the image to generate N sequences of RSVP image chips, and the N sequences of RSVP image chips are concatenated.

In another aspect, the system removes a RSVP image chip from the sequence of the plurality of RSVP image chips if a posterior probability of the RSVP chip is equal to or above a predetermined threshold, thereby generating a plurality of remaining RSVP image chips. The system then performs N staggered raster scans of the image to generate N sequences of RSVP image chips from the remaining RSVP image chips, and the N sequences of RSVP image chips are concatenated.

In another aspect, if a likelihood of the presence of a target of interest in one or more RSVP image chips is above a predetermined percentile, then the system spaces the one or more RSVP image chips that are above the predetermined percentile between a plurality of RSVP image chips that are below the predetermined percentile.

In another aspect, the present invention is a RSVP system comprising one or more processors and a non-transitory computer-readable medium having executable instructions encoded thereon such that when executed, the one or more processors perform multiple operations. The system receives a sequence of a plurality of rapid serial visual presentation (RSVP) image chips having an order, wherein the RSVP image chips are generated from an image via a pre-processing step and have a high probability of containing a target of interest. The system then alters the order of the sequence of the plurality of RSVP image chips to increase the probability of detection of a true target of interest when presented to a human subject. The RSVP system further comprises a visual display for presenting the plurality of RSVP image chips to the human subject, and at least one electoencephalography (EEG) sensor for measuring brain activity of the human subject.

In another aspect, the present invention also comprises a method for causing a processor to perform the operations described herein.

Finally, in yet another aspect, the present invention also comprises a computer program product comprising computer-readable instructions stored on a non-transitory computer-readable medium that are executable by a computer having a processor for causing the processor to perform the operations described herein.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to a system for rapid object detection and, more particularly, to a system for rapid object detection that optimizes rapid serial visual presentation (RSVP) spacing and fusion. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter-clockwise have been used for convenience purposes only and are not intended to imply any particular fixed direction. Instead, they are used to reflect relative locations and/or directions between various portions of an object. As such, as the present invention is changed, the above labels may change their orientation.

Before describing the invention in detail, first a list of cited literature references used in the description is provided. Next, a description of various principal aspects of the present invention is provided. Subsequently, an introduction provides the reader with a general understanding of the present invention. Finally, specific details of the present invention are provided to give an understanding of the specific aspects.

(1) LIST OF INCORPORATED CITED LITERATURE REFERENCES

The following references are cited throughout this application. For clarity and convenience, the references are listed herein as a central resource for the reader. The following references are hereby incorporated by reference as though fully included herein. The references are cited in the application by referring to the corresponding literature reference number, as follows:
1. Deepak Khosla; Rajan Bhattacharyya; Penn Tasinga; David J. Huber;
   Optimal detection of objects in images and videos using electroencephalography (EEG). Proc. SPIE 8050, Signal Processing, Sensor Fusion, and Target Recognition XX, 80501C (May 4, 2011).
2. Raymond J. E., Shapiro K. L., Anmell K. M., "Temporary suppression of visual processing in an RSVP task: an attentional blink?", Journal of experimental psychology. Human perception and performance 18 (3): 849-60 (1992).
3. Thorpe et al., "Speed of Processing in the Human Visual System", Nature, vol. 381, pp. 520-522, 1996.

(2) PRINCIPAL ASPECTS

The present invention has three "principal" aspects. The first is a system for rapid object detection. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

Figure 1:
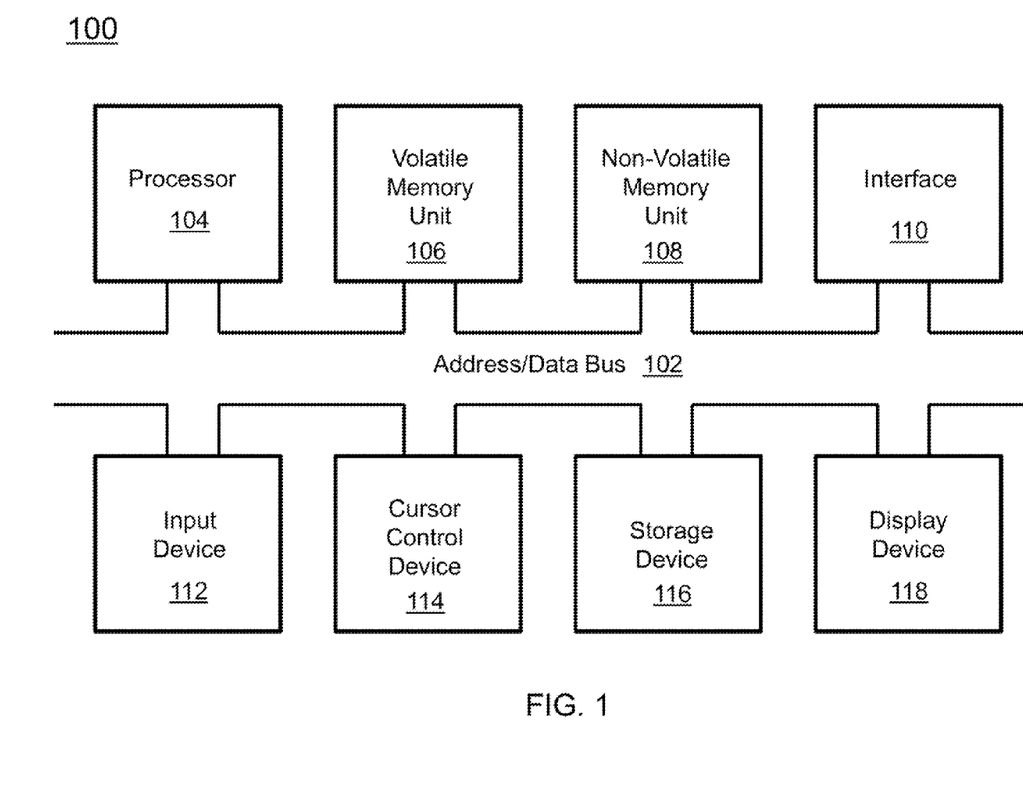
FIG. 1 is a block diagram depicting the components of a system for rapid object detection according to the principles of the present invention.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, or a field programmable gate array.

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 16 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
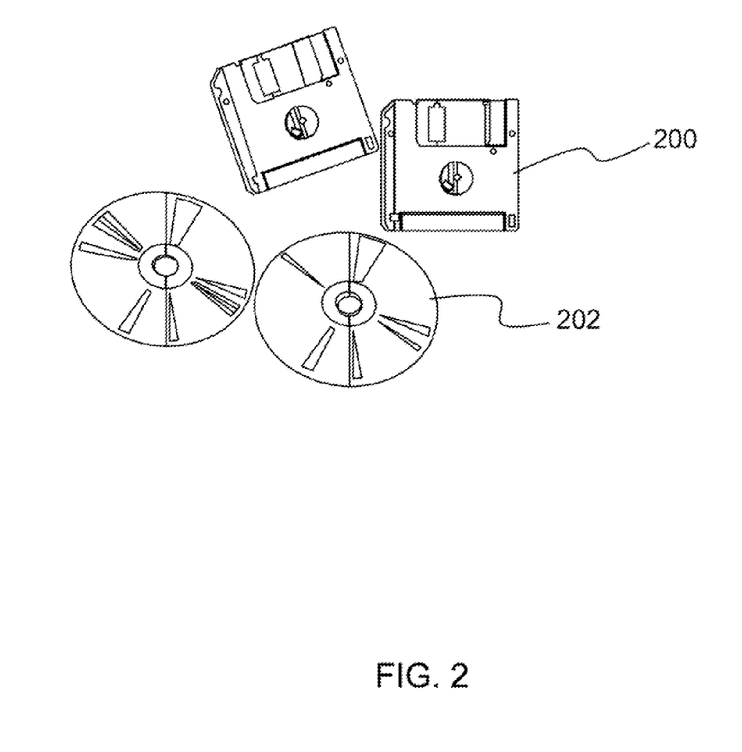
FIG. 2 is an illustration of a computer program product according to the principles of the present invention.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) INTRODUCTION

Random serial visual presentation (RSVP) measures the brain activity of a human subject while watching a stream of rapid images via a visual display (e.g., computer monitor, television) in order to find incongruities and inconsistencies in the images (i.e., "targets"). The RSVP protocol has recently been used as a powerful tool for high-throughput filtering of images into simple "target" and "non-target" categories, as described in Literature Reference No. 3. This involves presenting, via a display (e.g., monitor), a series of small images (e.g., at 256-by-256 pixel resolution), sometimes called "chips", to a human subject at a very high frame rate (e.g., 10 Hertz) and measuring the electrical activity of the subject's brain using electroencephalograph (EEG) technology. During a RSVP experiment, the images presented to the human subject are typically randomized.

The user's brain signals, measured via at least one EEG sensor, during visualization of the RSVP are analyzed to detect a P300 signal. The P300 neural signal is a specific brainwave which occurs at a specific and fixed time delay (e.g., 25-500 milliseconds) from the presentation of the image. The P300 signal is far more reliable than voluntary responses of subjects, such as button presses, which exhibit variable delays. This signal occurs as the result of a "surprise", which can be the result of seeing a target in an image mixed with many non-targets in the RSVP sequence. A neural score is computed for each image in the sequenced set of images based on the existence and strength of the P300 signal. The chips that are perceived as non-targets are considered "boring" and do not exhibit a P300 wave in the subject's EEG. Therefore, the presence of the P300 signal is a valuable discriminator between what the subject considers a "surprising" versus a "boring" chip.

The user EEG measurements collected during RSVP presentation are pre-processed via band-pass filtering in the desired frequency range (typically 1-100 Hz). The onset of presentation of each image (static case) or clip (video case) is also recorded, and this onset is used as a starting trigger to create user EEG data segments (or epochs) from the EEG measurements. Each user EEG data segment corresponds to each image presentation, is typically one second long, and contains the neural signatures of the desired visual response for that image presentation. Each user EEG data segment is then classified into one of two classes: segments that contain an item of interest or segments that do not contain the item of interest. In practice, each user EEG data segment is assigned a continuous score or likelihood of it belonging to each class.

The computation of an EEG score includes an explicit prior training step during which known images or clips of targets and non-targets are presented and the learning of features and classifiers in the corresponding user EEG data segments is carried out. The classifier is then employed to determine an EEG score. This learning can be done using a set of classifier parameters, non-limiting examples of which include time series analysis, feature extraction, and classification methods. In an aspect described below, linear discrimination analysis of RSVP EEG data was used for classification of neural signatures into target and non-target images.

Once the learning is complete, the learned classifier is used for subsequent classification of the user EEG data segments. Thus, each user EEG data segment and its corresponding visual image are assigned a classification score, typically between 0 and 1, for each of the classes (i.e., item of interest or no item of interest). This score is the EEG score and is the final score. Based on the EEG score, the data segment (image chip) is classified as containing an IOI (item of interest) or not containing an IOI. High classification scores indicate a high likelihood of belonging to that class, and vice versa. Classification scoring is a common practice in all classifiers, and a threshold can be chosen to achieve a desired trade-off between true detections and false alarms to generate traditional Receiver Operating Characteristics (ROC) performance curves, if desired. This step can optionally further sort the potential IOI regions in descending order (e.g., highest scores first) based on classification scores of the IOI class.

(4) SPECIFIC DETAILS OF THE INVENTION

In other research groups, rapid serial visual presentation (RSVP) image chips are created from static images without an upfront cognitive process. This results in low density threats in RSVP. Comparatively, in the approach described herein a computer vision process filters the bulk of the non-target RSVP image chips out, presenting only RSVP image chips that have a high probability of containing a target to the user. Cognitive-neural methods for threat detection and RSVP optimization approaches have been previously described in Literature Reference No. 1 and U.S. Pat. No. 8,214,309, entitled, "Cognitive-Neural Method for Image Analysis," which is hereby incorporated by reference as though fully set forth herein. Challenges in the current state-of-the-art include high target density in RSVP and target bursts in RSVP. The first challenge is decoding P300 evoked response potentials (ERPs) degraded by the relatively high numbers of targets present in RSVP sequences.

Because the front-end computer vision (cognitive) processes filter out the vast majority of non-target chips, the density of targets in the RSVP sequences generated is likely to be high. The higher frequency of target occurrence has a negative impact on the probability of target detection due to the effects of habituation on the P300 ERP.

The second challenge is detecting targets that might not be perceived by the operator due to bursts of targets in RSVP sequences. After the cognitive process, chips are typically selected from high resolution video in a raster scan pattern. This has the benefit of reducing jarring contrasts between successive chips, such as the color and brightness differences between a chip of sky and a chip of shadowed ground. The raster scan has the disadvantage of often placing target chips together in an RSVP sequence when the targets they represent are closely clustered in a scene, or when targets move between chip areas during the time in which the system collects video for a single RSVP. If placed close enough together, often operators will not be able to perceive subsequent targets due to attentional blink resulting in false negatives in target classification.

Figure 3:
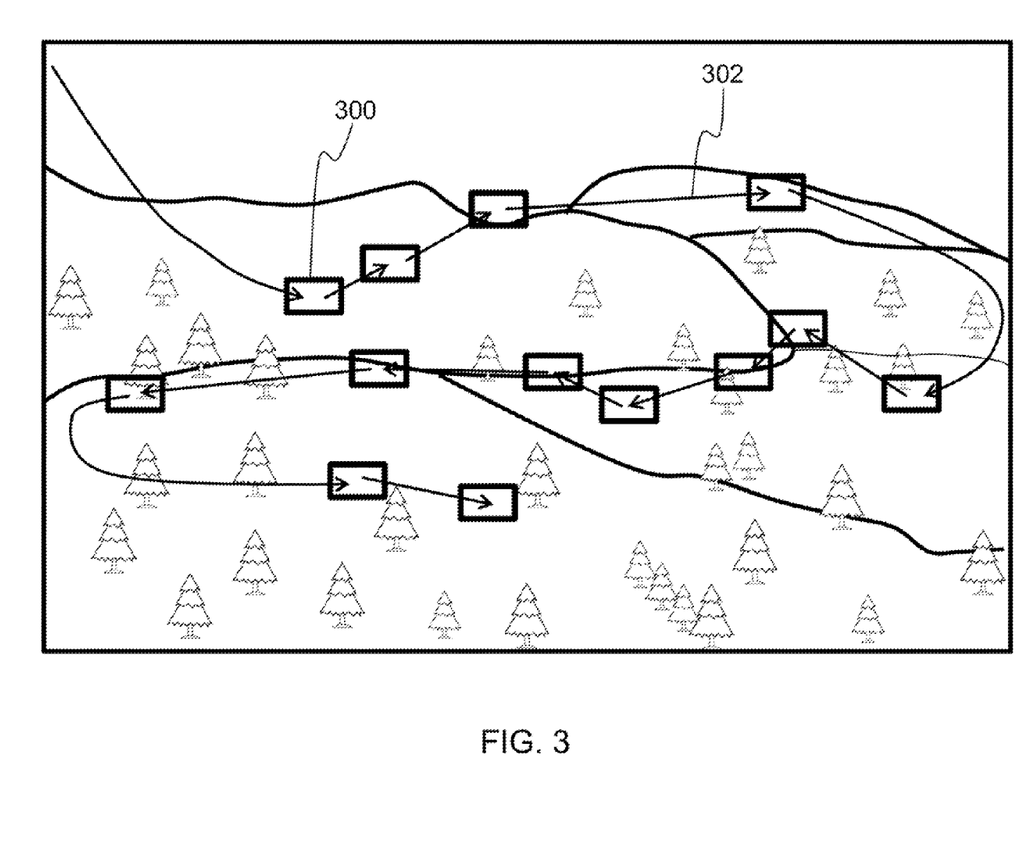
FIG. 3 illustrates a demonstration of the ordering of image chips in a rapid serial visual presentation (RSVP) according to a baseline single raster scan of the field-of-view.

FIG. 3 illustrates a demonstration of the ordering of chips in a RSVP according to a single raster scan of the field-of-view in a baseline approach. The identified clips are outlined by rectangles 300. The arrows 302 mark the order of clips displayed in the RSVP sequence. The raster scan sweeps the field-of-view approximately from left to right and then right to left alternately until the bottom of the field of view is reached.

Figure 4:
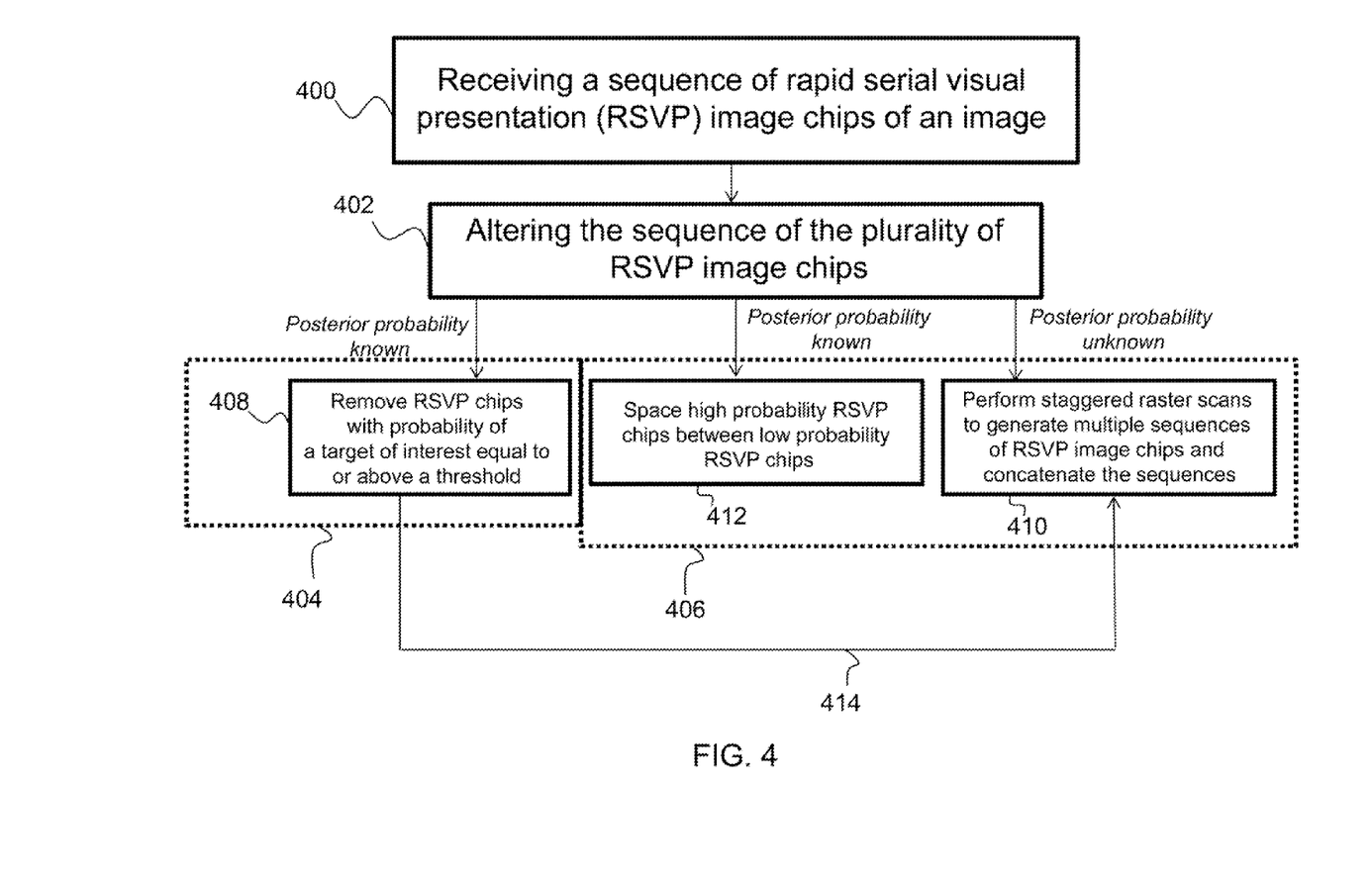
FIG. 4 is a flow chart depicting a system for optimal RSVP spacing and fusion according to the principles of the present invention.

The spacing processes according to the principles of the present invention address both the target density and bursting challenges. Furthermore, solutions to the bursting challenge are provided in two different circumstances, one in which the posterior of a target being present in a given chip is defined and one in which no such posterior is available, as illustrated in FIG. 4. In a first step 400, a sequence of RSVP image chips of an image having an order is received. In a second step 402, the order of the sequence of RSVP image chips is altered to increase the probability of detection of a true target of interest by a human subject. As described above, the system according to the principles of the present invention comprises solutions to address target density (represented by the dashed outline 404) and bursting behavior (represented by the dashed outline 406). A hybrid fusion solution comprises elements of both solutions.

To reduce target density if the posterior of a target being present in a given chip is available, RSVP image chips having a probability of a target of interest being present in the image chips equal to or above a predetermined threshold are removed in a first sub-step 408. To reduce bursting behavior if the posterior of a target being present is unknown, then staggered raster scans are performed to generate multiple sequences of RSVP image chips, and the sequences are concatenated in a second sub-step 410. To reduce bursting behavior if the posterior of a target is known, RSVP image chips having a high posterior probability are spaced between RSVP image chips having a low posterior probability in a third sub-step 412. In a hybrid fusion solution (represented by the arrow 414), RSVP image chips having a high posterior probability are removed (in a first sub-step 408) followed by the performance of staggered raster scans and concatenation of the sequences of RSVP image chips (in the second sub-step 410) to generate multiple sequences of RSVP image chips, and the sequences are concatenated (in the second sub-step 410). Each of these solutions will be described in further detail below.

(4.1) Reduction of Target Density in RSVP Sequences

If a posterior probability of a target being present in a given chip is known, the number of targets within an RSVP sequence can be reduced by removing RSVP chips with a target posterior probability above a given threshold. This threshold can be set according to the permissible false positive rate. Posterior probability refers to the revised probability of an event occurring after taking into consideration new information.

In the system described herein, a front-end cognitive computer vision process computes the probability of the presence of a target in a given chip with a relatively high detection rate, often scoring receiver operating characteristic area under the curve (Az) values of 0.9 or higher. Further, the top percentiles of these likelihoods often contain the bulk of the targets and allow few false positives. In a recent analysis of a field test, it was found that removing chips with target probabilities above a threshold of 0.53 eliminated 54.2% of the targets in the resultant RSVP sequences, while only admitting a 1.2% false positive rate. This reduced the average number of targets per 50 chip sequence from 6 to 2.75.

The reduction in the number of targets per RSVP sequence is predicted to alleviate the degradation of the P300 ERP associated with habituation effects. The ERPs resulting from the reduced sequences should be associated with a clearer signal that is easier to decode.

(4.2) Reduction of Bursting Behavior in RSVP Sequences

If the posterior of a target being present in a given chip is unknown, bursts of targets occurring in RSVP sequences compiled from raster scans can be reduced by performing several staggered raster scans and concatenating the resulting sequences end to end.

Without knowledge of the posterior probability that a chip contains a target, only prior assumptions on how the targets may occur in the world may be relied upon for assuaging bursting behavior. As observed in field tests, targets often cluster together in a scene or can move through multiple chip extraction areas, resulting in bursts of successive targets in resultant RSVP sequences. Based on this information, spacing chips drawn from adjacent chip extraction areas should reduce the occurrence of target bursts. By performing N raster scans each on each $n_i$th element (image chip), where $n_i$ is from the set $\{1, 2, \ldots, N\}$ starting with the $n_i$th element, N sequences were obtained with no two chips drawn from adjacent chip extraction areas. These sequences can then be concatenated end-to-end into a single sequence with only N−1 non-raster adjacencies.

Figure 5:
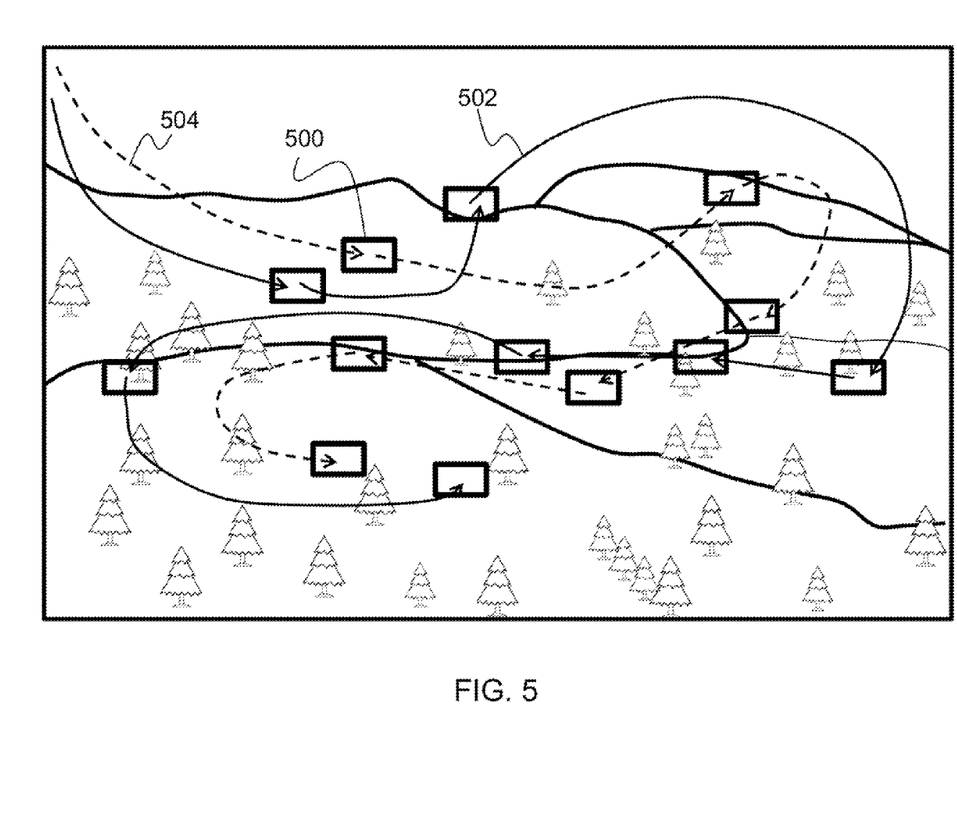
FIG. 5 illustrates a demonstration of the ordering of image chips in a RSVP according to two raster scans of the field-of-view according to the principles of the present invention.

FIG. 5 depicts a demonstration of the ordering of chips in a RSVP according to two raster scans (N=2) of the field-of-view. The identified chips are outlined in rectangles 500. The solid line arrows 502 mark the order of clips displayed in the RSVP sequence of the first raster scan. The dashed line arrows 504 mark the order of clips displayed in the RSVP sequence of the second raster scan. The final RSVP sequence is a concatenation of the two individual raster scan sequences.

Further, if the likelihood of the presence of a target in a given chip is known, there are alternative methods of reducing target bursts. Given a certain percentile of the known target likelihood observations, the chips associated with probabilities above this percentile can be spaced between blocks of chips with lower probabilities. An aspect of this is described below.

First, chips with probabilities in the high percentiles are stripped out of the sequence and placed in order into a FIFO (first in, first out) queue, Q1. The remaining chips with target likelihoods below the selected percentile are assembled in order into a second FIFO queue, Q2. A new sequence is iteratively built up by arranging elements from Q1 and Q2 such that elements of Q1 are maximally-apart from each other. One approach for doing this is by first popping N1 elements from Q1 and adding them in order into the new sequence, then popping an element from Q2 and adding it to the sequence until no elements are left in either queue according to the following:

$N1 = \text{floor}(\{\text{length}(Q2)/(\text{length}(Q1)\} + 1)$.

For instance, if length (Q1)=5, length (Q2)=20, then N1=floor((20/5)+1)=5. This means that one selects five images from Q2, one image from Q1, four images from Q2, one image from Q1, and repeat until the total sequence length is 25. This maximally spaces chips that have a high probability while padding the ends of the sequence with chips with a low probability of target occurrence. The targets can be added probabilistically in a similar fashion if the resultant RSVP sequences appear too structured to evoke P300 ERPs.

(4.3) Hybrid Fusion Approach

The hybrid fusion process described below leverages a combination of the target density and bursting reduction techniques described above. First, the target density is reduced by removing all RSVP chips with a target likelihood over or equal to a threshold (value between 0-1, e.g., 0.53) as described in the target density reduction section above. With most of the targets removed, the misclassified targets in the remaining shortened sequence need to be spaced. While intuitively it would seem that spacing these chips by target likelihood would produce the best results, in practice it was found that the remaining targets are often poorly estimated and, thereby, hard to identify and space based on their target probability. To work around this issue, multiple raster scans of the data (e.g., N=3) are performed, and the resulting sequences are concatenated into one.

Figure 6A:
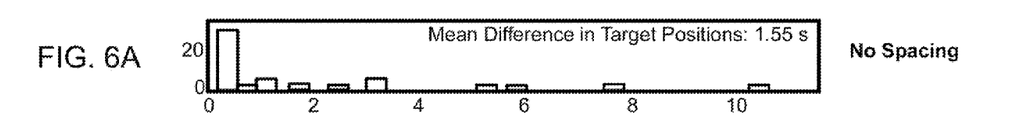
FIG. 6A illustrates histograms of the occurrences of spacing intervals with no spacing.
Figure 6B:
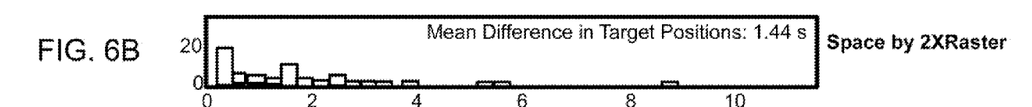
FIG. 6B illustrates histograms of the occurrences of spacing intervals with spacing by 2× raster according to the principles of the present invention.
Figure 6C:
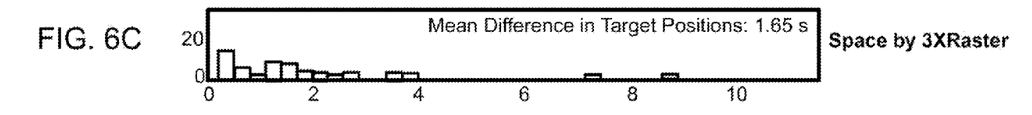
FIG. 6C illustrates histograms of the occurrences of spacing intervals with spacing by 3× raster according to the principles of the present invention.
Figure 6D:
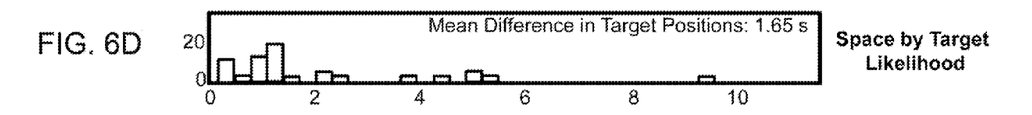
FIG. 6D illustrates histograms of the occurrences of spacing intervals with spacing by target likelihood according to the principles of the present invention.
Figure 6E:
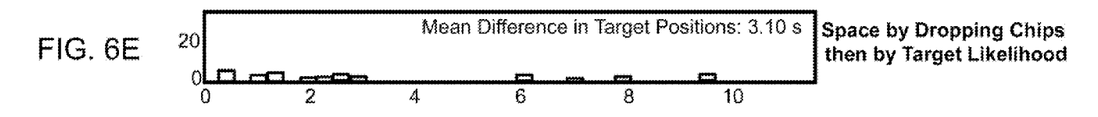
FIG. 6E illustrates histograms of the occurrences of spacing intervals with spacing by dropping image chips, then by target likelihood according to the principles of the present invention.
Figure 6F:
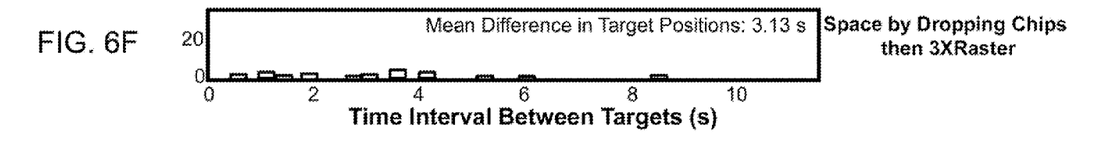
FIG. 6F illustrates histograms of the occurrences of spacing intervals with spacing by dropping chips, then 3× raster according to the principles of the present invention.

FIGS. 6A-6F illustrate histograms of the occurrences of spacing intervals between targets for each spacing process. FIG. 6A depicts results with no spacing (baseline), FIG. 6B depicts results with spacing by 2× raster, FIG. 6C depicts results with spacing by 3× raster, FIG. 6D depicts results with spacing by target likelihood, FIG. 6E depicts results with spacing by dropping chips, then by target likelihood, and FIG. 6F depicts results with spacing by dropping chips then 3× raster. As shown in FIGS. 6C and 6F, multiple raster scans of the data produces the best spacing results given the kind of data collected during an actual field test. Between FIGS. 6A-6C, FIG. 6C has the best spacing. Note the mean difference in target positions values (shown at top right of each plot) is 1.65 seconds (s) for FIG. 6C and is the maximum across FIGS. 6A-6C. Similarly, between FIGS. 6D-6F, FIG. 6F has the highest spacing at 3.13 s. FIGS. 6C and 6F use a 3× (multiple) raster scan approach and have the best spacing.

(4.4) Experimental Studies

In experimental studies, the goal was to demonstrate that better target detection could be achieved in a RSVP setting with P300-based EEG through the use of the spacing and reduction-of-target-density processes described herein. The stimuli used were extracted from video data recorded during field tests in Yuma, Ariz. Relevant chips were assembled from the video sets in accordance with target detection computer vision processes (examples of which are described in U.S. Pat. No. 8,214,309, U.S. Pat. No. 8,335,751, U.S. Pat. No. 8,363,939, and U.S. Pat. No. 8,369,652, which are hereby incorporated by reference as though fully set forth herein), which assigned prior probabilities to each chip. Once RSVP videos had been assembled, blocks that contained less than two targets were removed from the dataset. Videos with a very high target density were purposely chosen in order to highlight the benefit of the system according to the principles of the present invention.

A volunteer was fitted with EEG equipment and placed in front of a computer monitor, which displayed four sets of RSVP videos. The RSVP video sets consisted of a training set (50 blocks each containing 1 target and 49 non-targets), a set with no spacing (25 blocks each containing 24 clips), a set with 3-times raster scanning (applied to the same 25 blocks), and a set in which the clips with high prior probabilities were dropped using the heuristic threshold 0.52 and 3-times raster scanned (applied to the same 25 blocks).

The classifier was trained on EEG data recorded during the training set, then applied to EEG-data recorded during the three test sets. The area-under-curve (AUC) results of each test are displayed in Table 1 below.

TABLE 1

|  | Baseline | Spacing (Raster ×3) | Fusion (Threshold, Raster ×3) |
|---|---|---|---|
| AUC/Az | 0.6 | 0.64 | 0.72 |

In this case, the increased raster scanning (i.e., spacing (raster ×3) clearly improves the target detection over the normal unspaced (i.e., baseline) presentation. Furthermore, dropping clips and then raster scanning (i.e., fusion) has an even more dramatic increase in target detection. Note that the absolute Az values are still low in all cases, but that is because input videos with a very high target density were chosen in order to highlight the benefit of the present invention.

Table 2 below demonstrates the total number of targets in the presentation before (i.e., baseline) and after the dropping of high score threat clips (i.e., after thresholding (drop sure bets)).

TABLE 2

|  | Total Targets |
|---|---|
| Baseline | 242 |
| After thresholding (Drop Sure Bets) | 78 |

Figure 7A:
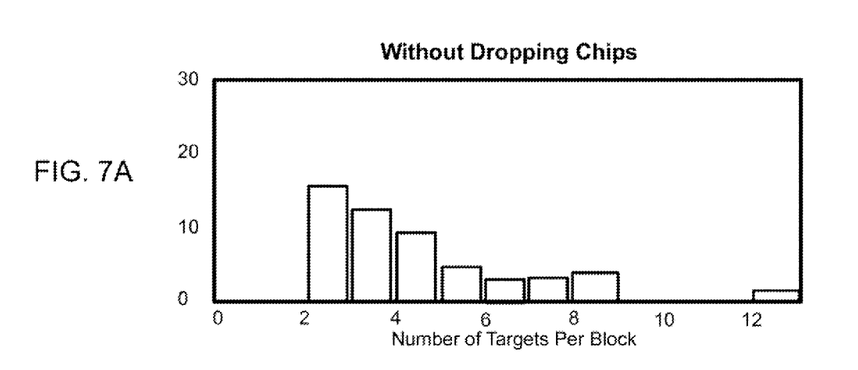
FIG. 7A illustrates histograms of the distribution of number of targets per image chip before dropping image chips.
Figure 7B:
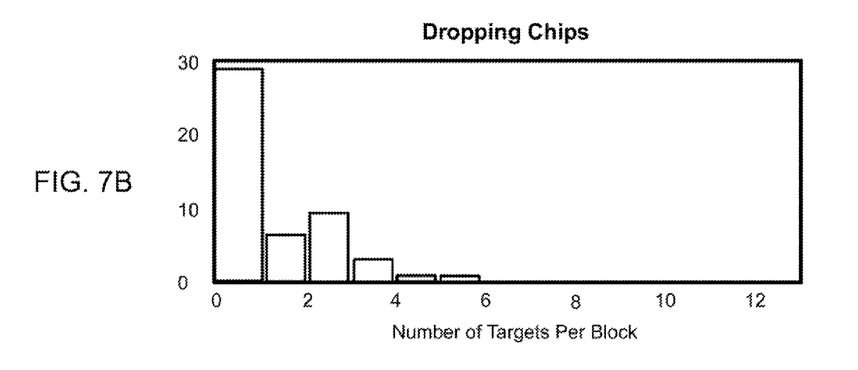
FIG. 7B illustrates histograms of the distribution of number of targets per image chip after dropping image chips according to the principles of the present invention.

FIGS. 7A and 7B show the distribution of number of targets per chip before and after dropping chips, respectively. Specifically, FIG. 7A depicts histograms of the number of targets per block before thresholding (dropping of high-scoring cognitive chips). FIG. 7B depicts histograms of the number of targets per block after thresholding. After thresholding, most blocks contain fewer targets (mostly 0-2 targets) as shown in FIG. 7B, while the average number of targets per block is closer to 4 in the baseline case shown in FIG. 7A.

Figure 8A:
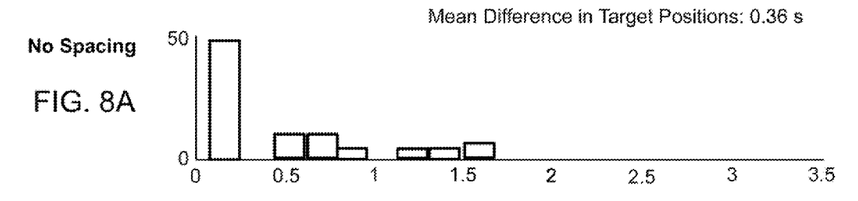
FIG. 8A illustrates histograms of the occurrences of spacing intervals between targets for no spacing.
Figure 8B:
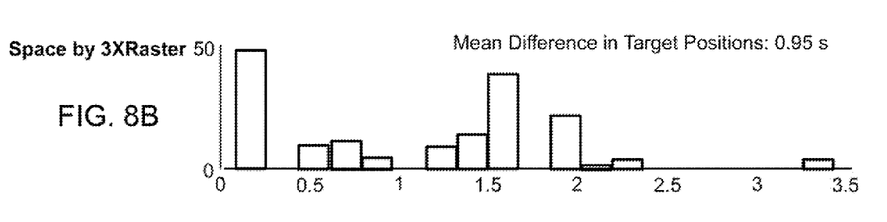
FIG. 8B illustrates histograms of the occurrences of spacing intervals between targets for spacing by 3× raster according to the principles of the present invention.
Figure 8C:
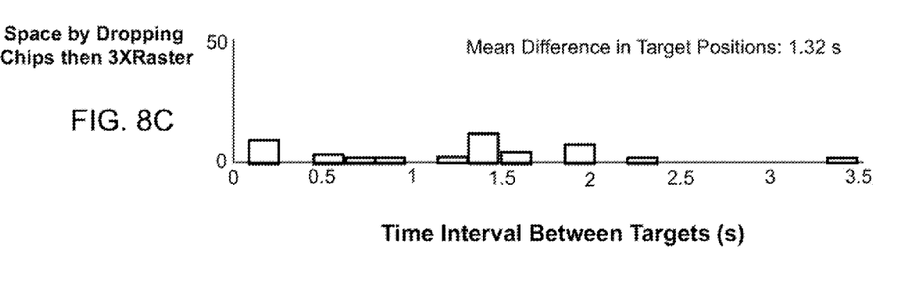
FIG. 8C illustrates histograms of the occurrences of spacing intervals between targets for spacing by dropping image chips, then 3× raster according to the principles of the present invention.

Finally, FIGS. 8A-8C illustrate histograms of the occurrences of spacing intervals between "true" targets for each spacing process for experimental studies of the present invention. A true target is an object/event designated and ground-truthed as a target during a field test (e.g., a dismount moving around a tree). FIG. 8A depicts no spacing (baseline) results, FIG. 8B depicts space by 3× raster, and FIG. 8C depicts space by dropping chips then 3× raster. Note that the baseline spacing (FIG. 8A) is 0.36 seconds, while the fusion spacing (FIG. 8C) is 1.32 seconds. This reduced spacing translates into better threat detection of Az=0.72, compared to baseline Az=0.6.

The system according to the principles of the present invention is useful for any application that employs the RSVP paradigm for rapid object detection. As a non-limiting example, it can be employed in human-assisted threat assessment and threat queuing applications in which the system must scan a wide field-of-view and report any anomalies to the landscape. In these instances, automated classification methods might fail. Other examples of potential applications include automotive (passive and active) safety, factory safety and efficiency (e.g., sorting tasks), intelligence analysis, surveillance, and automated driving.

What is claimed is:

1. A system for rapid serial visual presentation (RSVP) spacing and fusion, the system comprising:
   one or more processors and a non-transitory computer-readable medium having executable instructions encoded thereon such that when executed, the one or more processors perform operations of:
   receiving a sequence of a plurality of rapid serial visual presentation (RSVP) image chips having an order, wherein the plurality of RSVP image chips are generated from an image via a pre-processing step and have a high probability of containing a target of interest; and
   altering the order of the sequence of the plurality of RSVP image chips to increase the probability of detection of a true target of interest when presented to a human subject.

2. The system as set forth in claim 1, wherein if a posterior probability of a RSVP image chip containing a target of interest is known, then the one or more processors further perform an operation of removing the RSVP image chip from the sequence of the plurality of RSVP image chips if the posterior probability of the RSVP chip is equal to or above a predetermined threshold.

3. The system as set forth in claim 2, wherein the predetermined threshold is set according to a permissible false positive rate.

4. The system as set forth in claim 1, wherein the one or more processors further perform operations of:
   performing N staggered raster scans of the image to generate N sequences of RSVP image chips; and
   concatenating the N sequences of RSVP image chips.

5. The system as set forth in claim 1, wherein the one or more processors further perform operations of:
   removing a RSVP image chip from the sequence of the plurality of RSVP image chips if a posterior probability of the RSVP chip is equal to or above a predetermined threshold, thereby generating a plurality of remaining RSVP image chips;
   performing N staggered raster scans of the image to generate N sequences of RSVP image chips from the remaining RSVP image chips; and
   concatenating the N sequences of RSVP image chips.

6. The system as set forth in claim 1, wherein if a likelihood of the presence of a target of interest in one or more RSVP image chips is above a predetermined percentile, then the one or more processors perform an operation of spacing the one or more RSVP image chips that are above the predetermined percentile between a plurality of RSVP image chips that are below the predetermined percentile.

7. A computer-implemented method for rapid serial visual presentation (RSVP) spacing and fusion, comprising:
   an act of causing one or more processors to execute instructions stored on a non-transitory memory such that upon execution, the one or more processors perform operations of:
   receiving a sequence of a plurality of rapid serial visual presentation (RSVP) image chips having an order, wherein the plurality of RSVP image chips are generated from an image via a pre-processing step and have a high probability of containing a target of interest; and
   altering the order of the sequence of the plurality of RSVP image chips to increase the probability of detection of a true target of interest when presented to a human subject.

8. The method as set forth in claim 7, wherein if a posterior probability of a RSVP image chip containing a target of interest is known, then the one or more processors further perform an operation of removing the RSVP image chip from the sequence of the plurality of RSVP image chips if the posterior probability of the RSVP chip is equal to or above a predetermined threshold.

9. The method as set forth in claim 8, wherein the predetermined threshold is set according to a permissible false positive rate.

10. The method as set forth in claim 7, wherein the one or more processors further perform operations of:
    performing N staggered raster scans of the image to generate N sequences of RSVP image chips; and
    concatenating the N sequences of RSVP image chips.

11. The method as set forth in claim 7, wherein the one or more processors further perform operations of:
    removing a RSVP image chip from the sequence of the plurality of RSVP image chips if a posterior probability of the RSVP chip is equal to or above a predetermined threshold, thereby generating a plurality of remaining RSVP image chips;
    performing N staggered raster scans of the image to generate N sequences of RSVP image chips from the remaining RSVP image chips; and
    concatenating the N sequences of RSVP image chips.

12. The method as set forth in claim 7, wherein if a likelihood of the presence of a target of interest in one or more RSVP image chips is above a predetermined percentile, then the one or more processors perform an operation of spacing the one or more RSVP image chips that are above the predetermined percentile between a plurality of RSVP image chips that are below the predetermined percentile.

13. A computer program product for rapid serial visual presentation (RSVP) spacing and fusion, the computer program product comprising computer-readable instructions stored on a non-transitory computer-readable medium that are executable by a computer having a processor for causing the processor to perform operations of:
    receiving a sequence of a plurality of rapid serial visual presentation (RSVP) image chips having an order, wherein the plurality of RSVP image chips are generated from an image via a pre-processing step and have a high probability of containing a target of interest; and altering the order of the sequence of the plurality of RSVP image chips to increase the probability of detection of a true target of interest when presented to a human subject.

14. The computer program product as set forth in claim 13, wherein if a posterior probability of a RSVP image chip containing a target of interest is known, then the one or more processors further perform an operation of removing the RSVP image chip from the sequence of the plurality of RSVP image chips if the posterior probability of the RSVP chip is equal to or above a predetermined threshold.

15. The computer program product as set forth in claim 14, wherein the predetermined threshold is set according to a permissible false positive rate.

16. The computer program product as set forth in claim 13, further comprising instructions for causing the processor to perform operations of:

performing N staggered raster scans of the image to generate N sequences of RSVP image chips; and concatenating the N sequences of RSVP image chips.

17. The computer program product as set forth in claim 13, further comprising instructions for causing the processor to perform operations of:

removing a RSVP image chip from the sequence of the plurality of RSVP image chips if a posterior probability of the RSVP chip is equal to or above a predetermined threshold, thereby generating a plurality of remaining RSVP image chips;

performing N staggered raster scans of the image to generate N sequences of RSVP image chips from the remaining RSVP image chips; and concatenating the N sequences of RSVP image chips.

18. The computer program product as set forth in claim 13, wherein if a likelihood of the presence of a target of interest in one or more RSVP image chips is above a predetermined percentile, then the one or more processors perform an operation of spacing the one or more RSVP image chips that are above the predetermined percentile between a plurality of RSVP image chips that are below the predetermined percentile.

19. A rapid serial visual presentation (RSVP) system, the system comprising:

one or more processors and a non-transitory computer-readable medium having executable instructions encoded thereon such that when executed, the one or more processors perform operations of:

receiving a sequence of a plurality of rapid serial visual presentation (RSVP) image chips having an order, wherein the plurality of RSVP image chips are generated from an image via a pre-processing step and have a high probability of containing a target of interest; and altering the order of the sequence of the plurality of RSVP image chips to increase the probability of detection of a true target of interest when presented to a human subject;

a visual display for presenting the plurality of RSVP image chips to the human subject; and at least one electoencephalography (EEG) sensor for measuring brain activity of the human subject.

* * * * *